United States Patent
Hobbs

(10) Patent No.: US 11,241,906 B1
(45) Date of Patent: Feb. 8, 2022

(54) FIDGET DEVICE

(71) Applicant: Jennifer Hobbs, Tomball, TX (US)

(72) Inventor: Jennifer Hobbs, Tomball, TX (US)

(*) Notice: Subject to any disclaimer, the term of this patent is extended or adjusted under 35 U.S.C. 154(b) by 0 days.

(21) Appl. No.: 16/742,724

(22) Filed: Jan. 14, 2020

Related U.S. Application Data

(60) Provisional application No. 62/792,364, filed on Jan. 14, 2019.

(51) Int. Cl.
| | |
|---|---|
| *B43K 29/00* | (2006.01) |
| *B43K 5/00* | (2006.01) |
| *A61M 21/02* | (2006.01) |
| *A63H 33/00* | (2006.01) |
| *A61M 21/00* | (2006.01) |

(52) U.S. Cl.
CPC ............. *B43K 29/00* (2013.01); *A61M 21/02* (2013.01); *A63H 33/00* (2013.01); *B43K 5/005* (2013.01); *A61M 2021/0022* (2013.01)

(58) Field of Classification Search
CPC ...... B43K 29/00; B43K 5/005; B43K 29/002; B43K 29/004; B43K 29/005; B43K 29/007; B43K 29/20; A61M 21/02; A61M 2021/00222; A61M 2021/0027; A61M 21/00; A63H 33/00; A63H 33/006; A63H 37/00
USPC .............................. 401/52, 195; 446/418, 419
See application file for complete search history.

(56) References Cited

U.S. PATENT DOCUMENTS

| | | | | |
|---|---|---|---|---|
| 1,730,257 A | * | 10/1929 | Welch | A44C 17/007 63/32 |
| 4,366,956 A | * | 1/1983 | Kifferstein | A63B 69/0028 446/419 |
| 5,328,172 A | * | 7/1994 | Jagiella | A63F 7/048 273/144 B |
| 5,366,125 A | * | 11/1994 | Procido | A47K 5/00 206/77.1 |
| 6,056,464 A | * | 5/2000 | Cohen | B43K 23/08 401/195 |
| 6,698,960 B2 | * | 3/2004 | Noguchi | B43K 29/003 401/195 |
| D667,176 S | * | 9/2012 | Crane | D30/160 |
| 9,950,556 B1 | | 4/2018 | Laemle et al. | |
| 2005/0163555 A1 | | 7/2005 | Cetera | |
| 2016/0232804 A1 | | 8/2016 | Nichols et al. | |
| 2017/0136805 A1 | | 5/2017 | Hoffman | |

* cited by examiner

*Primary Examiner* — David J Walczak
(74) *Attorney, Agent, or Firm* — Crose Law LLC; Bradley D. Crose

(57) ABSTRACT

A fidget device is configured to direct a user to engage in a stress-release activity and direct nervous energy in a manner to not created distraction and noise. The technology provides a fidget device having a movable, manipulable object disposed within a sleeve that a user can move back-and-forth and otherwise manipulate through movement within the sleeve. In at least one embodiment, the fidget device is a pen having a marble or ball within the sleeve that is manipulable by the user holding the pen as a fidget device.

17 Claims, 6 Drawing Sheets

FIDGET DEVICE

CROSS-REFERENCE TO RELATED APPLICATION(S)

The present non-provisional patent application claims the benefit of priority of U.S. Provisional Patent Application No. 62/792,364 which is entitled "FIDGET DEVICE", which was filed on Jan. 14, 2019, and which is incorporated in full by reference herein.

FIELD OF THE INVENTION

The technology described herein relates generally to sensory devices, fidget toys, gadget toys, stress release devices, and sensory manipulative devices. More specifically, this technology relates to a fidget device having a movable, manipulable object disposed within a sleeve that a user can move back-and-forth and otherwise manipulate through movement within the sleeve. Furthermore, this technology relates to a fidget device configured to direct a user engage in a stress-release activity and direct nervous energy in a manner to not create distraction and noise.

BACKGROUND OF THE INVENTION

Sensory devices, fidget toys, gadget toys, stress release devices, and sensory manipulative devices can help persons direct nervous energy. Such devices can be used to aid attention, focus, calming, listening, and otherwise directing nervous energy. Many attempts have been made in the background prior art to improve upon basic sensory devices, fidget toys, gadget toys, stress release devices, sensory manipulative devices, and the like. There remain many shortcomings and deficiencies with those known devices in the background art.

Related patents known in the art include the following:

U.S. Pat. No. 9,950,556, issued to Laemle et al. on Apr. 24, 2018 discloses a writing instrument that reduces impact of attention deficit disorders. A writing instrument includes an elongated body with a first end and a second end, wherein the first end is coupled to a post and the second end has an aperture for a writing tip to be exposed, a rotary bearing coupled to the post, wherein the rotary bearing has a central opening and wherein the post at least partially extends through the central opening of the rotary bearing, and a rotary device coupled to the bearing.

Related patent application publications known in the art include the following:

U.S. Patent Application Publication No. 2005/0163555, filed by Cetera and published on Jul. 28, 2005, discloses a pen clip with a slidable member. A clip comprises a slidable member upon a track. The clip may be attached to, for example, a handheld instrument, such as a pen. The slidable member moves along the track stimulating the tactile senses of the user and allows the user to dispel nervous tension. Indicia, such as advertising, may be placed upon the slidable member. Also disclosed is a method of getting the attention of a consumer by use of this clip with a slidable member.

U.S. Patent Application Publication No. 2016/0232804, filed by Nichols et al. and published on Aug. 11, 2016, discloses a fidget sleeve. The fidget sleeve includes an elongate hollow tube having two or more fidgets molded onto or attached to an outside surface of said tube. The tube can be slipped over a smooth elongated base object, such as a pencil or similar object, to provide manipulatives for students.

U.S. Patent Application Publication No. 2017/0136805, filed by Hoffman and published on May 18, 2017, discloses a pen clip with a slidable member. The writing instrument comprises a writing instrument base and a focus tool. The writing instrument base includes a marking system coupled with a barrel. The marking system is configured to provide writings on a writing medium, such as paper. The focus tool is coupled with the writing instrument base. The focus tool is configured to blend in with the writing base. The focus tool includes a device that engages a user's senses and reduces the negative impact of attention deficit disorders when used by the user. The fidget tool stimulates the user's vestibular system and proprioceptive senses through one or more of the following: movement, sound, smell, visual, and tactile action. The fidget tool may be discreet such that the tool is hidden or not viewable when not in use.

The foregoing patent and other information reflect the state of the art of which the inventor is aware and are tendered with a view toward discharging the inventor's acknowledged duty of candor in disclosing information that may be pertinent to the patentability of the technology described herein. It is respectfully stipulated, however, that the foregoing patent and other information do not teach or render obvious, singly or when considered in combination, the inventor's claimed invention.

BRIEF SUMMARY OF THE INVENTION

In various exemplary embodiments, the technology described herein provides a fidget device configured to direct a user to engage in a stress-release activity and direct nervous energy in a manner to not create distraction and noise. The technology provides a fidget device having a movable, manipulable object disposed within a sleeve that a user can move back-and-forth and otherwise manipulate through movement within the sleeve.

In one exemplary embodiment, the technology described herein provides a fidget device having an outer sleeve and a movable, manipulable object disposed within the outer sleeve that a holder of the fidget device can move back-and-forth and otherwise manipulate through movement within the sleeve.

The fidget device is configured to direct a user to engage in a stress-release activity and direct nervous energy in a manner to not create distraction and noise while used to aid attention, focus, calming, listening, and otherwise directing nervous energy.

In at least one embodiment, the fidget device is a traditional pen used for writing that is additionally configured as a fidget device.

In at least one embodiment, the fidget device is a writing instrument, such as a pen, with a small movable object, such as a marble, disposed within that is used to roll in a back-and-forth motion with the fingers of the device holder to relieve stress and nervous energy.

In at least one embodiment, the fidget device also provides that the movable object is disposed within a woven mesh sleeve. A user or holder of the device can push the movable object, such as a marble, back and forth or squish the sleeve together to roll the object around with fingers, thereby to direct nervous energy in a less distracting way and in a more socially appropriate way.

In various alternative embodiments, the fidget device can be a pen, mechanical pencil, highlighter, marker, stylus, laser pointer, and so forth.

In at least one embodiment, the fidget device is non-retractable.

In at least one embodiment, the fidget device is retractable, wherein the ball goes through the ink cartridge depending on whether it is a short or long ink cartridge.

In at least one embodiment, the fidget device includes more than one movable object disposed within, and they are all the same in size and shape.

In at least one embodiment, the fidget device includes more than one movable object disposed within, and they are all varied in size and shape.

In at least one embodiment, the fidget pen writing device is half twist.

In at least one embodiment, the fidget pen writing device is tip twist.

In at least one embodiment, the fidget device is twisted at any location of the device.

In at least one embodiment, the fidget device is integrally formed and all one piece with the exception of the movable object disposed within.

In at least one embodiment, the fidget device includes refillable ink.

In at least one embodiment, the fidget device includes non-refillable ink.

In at least one embodiment, the fidget device includes a cap.

In at least one embodiment, the fidget device does not include a cap.

In at least one embodiment, the sleeve of the fidget device is interchangeable.

In various embodiments, the sleeve can twist, screw, or clip on.

In various embodiments, the sleeve is flexible and can bend, roll, twist, or squish, or provide more than one of these functions.

In at least one embodiment, the sleeve is mesh.

In at least one embodiment, the fidget device is foldable.

In at least one embodiment, the fidget device includes an outer sleeve with mesh, or the like, disposed within and within the mesh the movable object is disposed.

Advantageously, the technology described herein provides a fidget device in combination with an always-useful writing device.

Also advantageously, the technology described herein provides a fidget device that aids the user or holder and relieves stress, pressure, boredom, anxiety, nail biting, frustration, and so forth.

Further advantageously, the technology described herein provides a fidget device having a unique movement of a marble, or like movable object, within the writing device.

Further advantageously, the technology described herein provides a fidget device that appears as a traditional writing instrument, such as a pen, and does not appear as a toy or like device.

Further advantageously, the technology described herein provides a fidget device that in combination with the writing instrument provides two devices in one without the need for the user or holder to set down one object and pick up another. The device can change mode by the user while in the user's hand. Writing one moment. Stress relief the next.

Further advantageously, the technology described herein provides a fidget device that does not create loud noises or distracting motions, pops, clicks, or the like. By way of comparison, many fidget devices make clicking noises and have spinners, clickers, switches, and the like.

There has thus been outlined, rather broadly, the more important features of the technology in order that the detailed description thereof that follows may be better understood, and in order that the present contribution to the art may be better appreciated. There are additional features of the technology that will be described hereinafter, and which will form the subject matter of the claims appended hereto. In this respect, before explaining at least one embodiment of the technology in detail, it is to be understood that the invention is not limited in its application to the details of construction and to the arrangements of the components set forth in the following description or illustrated in the drawings. The technology described herein is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the technology described herein.

Further objects and advantages of the technology described herein will be apparent from the following detailed description of a presently preferred embodiment which is illustrated schematically in the accompanying drawings.

BRIEF DESCRIPTION OF THE DRAWINGS

The technology described herein is illustrated with reference to the various drawings, in which like reference numbers denote like device components and/or method steps, respectively, and in which.

DETAILED DESCRIPTION OF THE INVENTION

Figure 1:
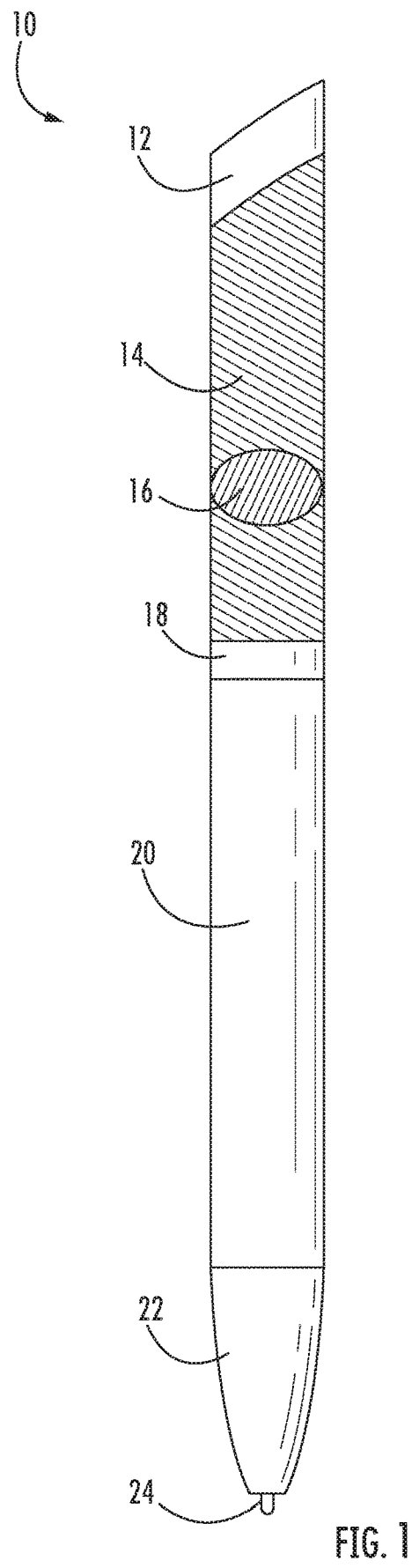
FIG. 1 is a front view of a fidget device, illustrating, in particular, a movable, manipulable object disposed within a sleeve of a writing instrument, such as a pen or pencil, that a holder of the device can move back-and-forth and otherwise manipulate through movement within the sleeve, according to an embodiment of the invention.
Figure 2:
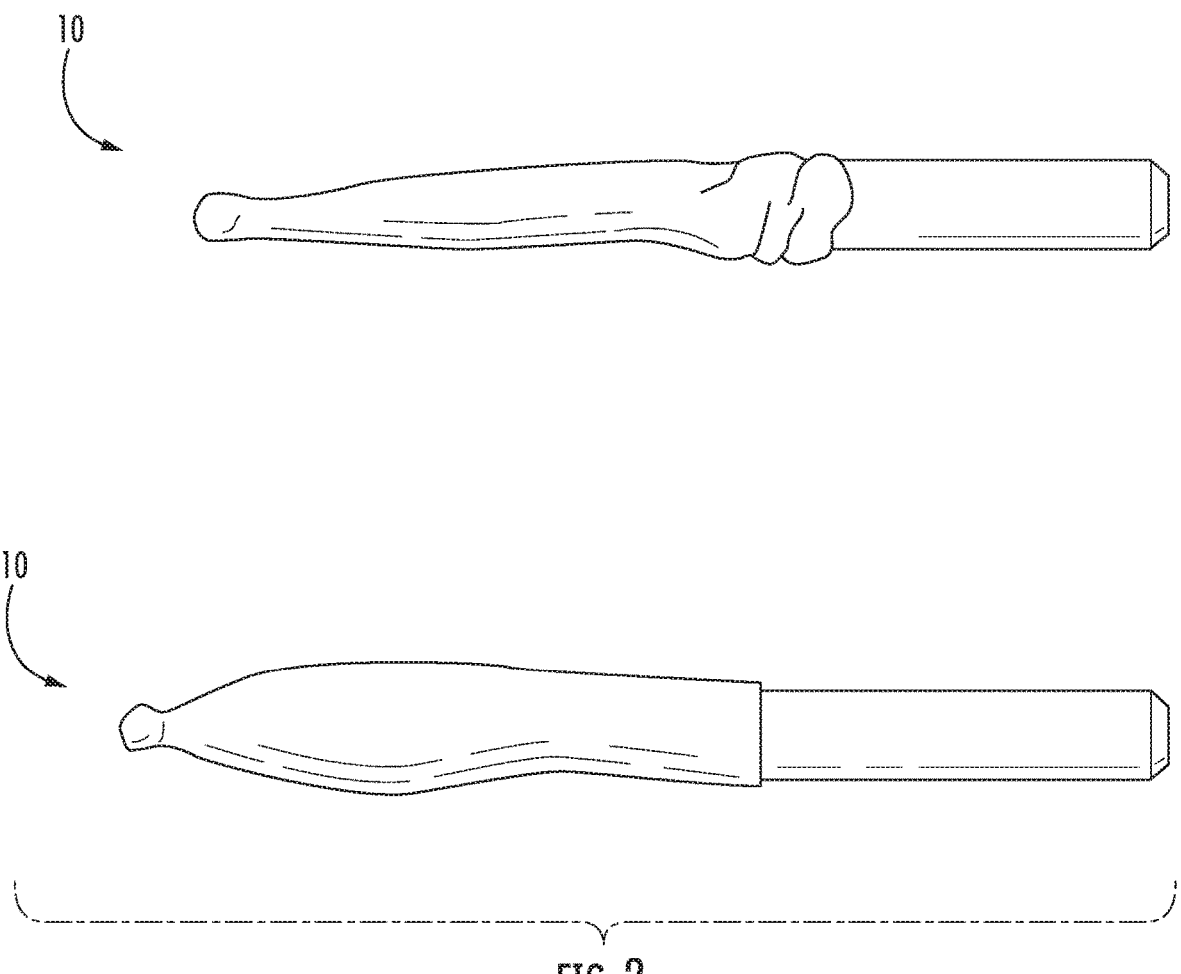
FIG. 2 is a top view of two fidget devices, illustrating, in particular, mesh sleeves and a movable, manipulable object disposed within the sleeves of the writing instruments that a holder of either device can move back-and-forth and otherwise manipulate through movement within the sleeve, according to an embodiment of the invention.
Figure 3:
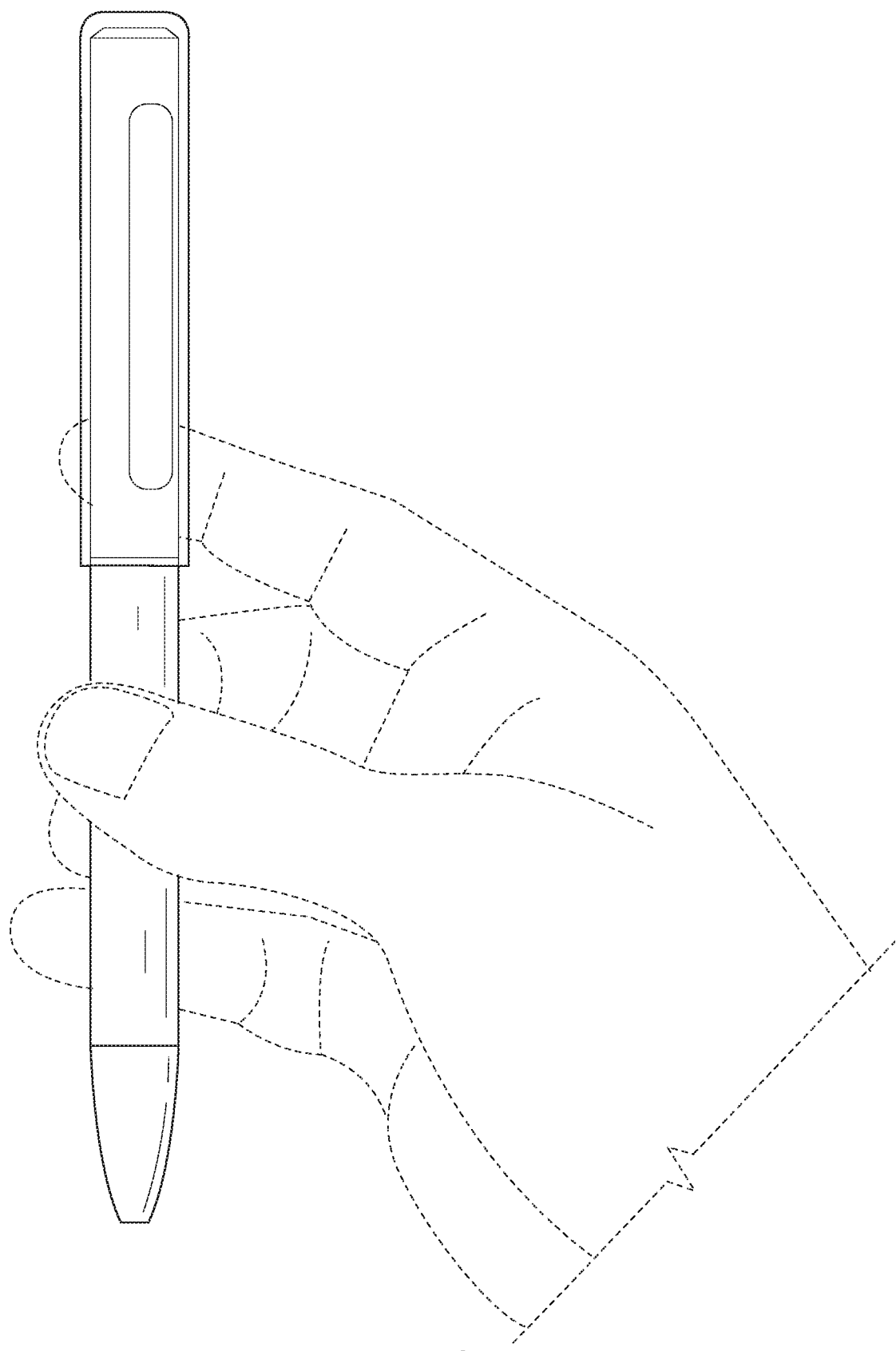
FIG. 3 is a front view of a fidget device, illustrating, in particular, a movable, manipulable object disposed within a sleeve of the writing instrument that a holder of the device can rotate the sleeve and move back-and-forth and otherwise manipulate through movement within the sleeve, according to an embodiment of the invention.
Figure 4:
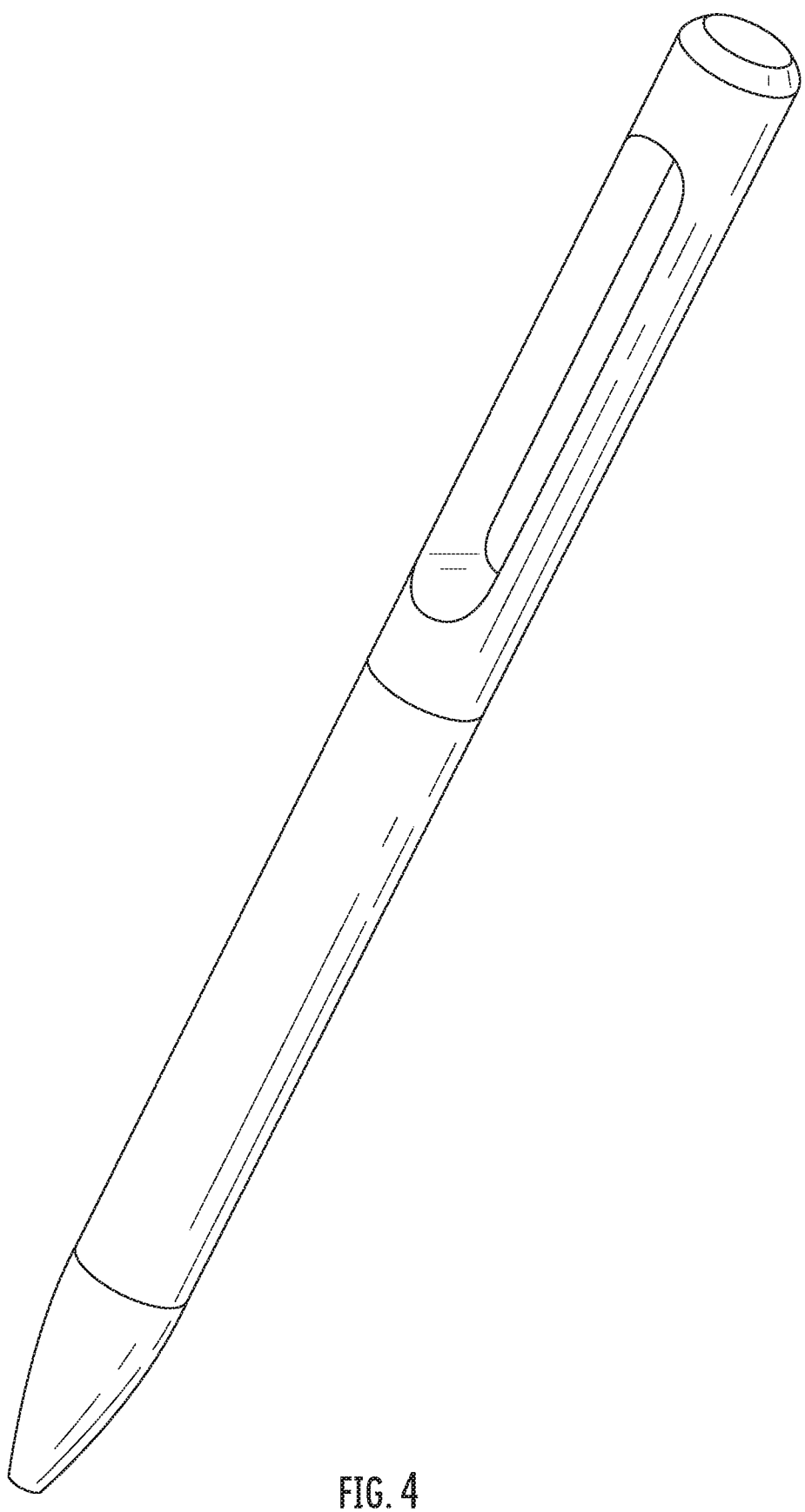
FIG. 4 is a front perspective view of a fidget device, illustrating, in particular, a movable, manipulable object disposed within a sleeve of the writing instrument, such as a pen, that a holder of the device can move back-and-forth and otherwise manipulate through movement within the sleeve, according to an embodiment of the invention.
Figure 5:
FIG. 5 is a front view of a fidget device, illustrating, in particular, a movable, manipulable object disposed within a sleeve of the writing instrument that a holder of the device can move back-and-forth and otherwise manipulate through movement within the sleeve, according to an embodiment of the invention.
Figure 6:
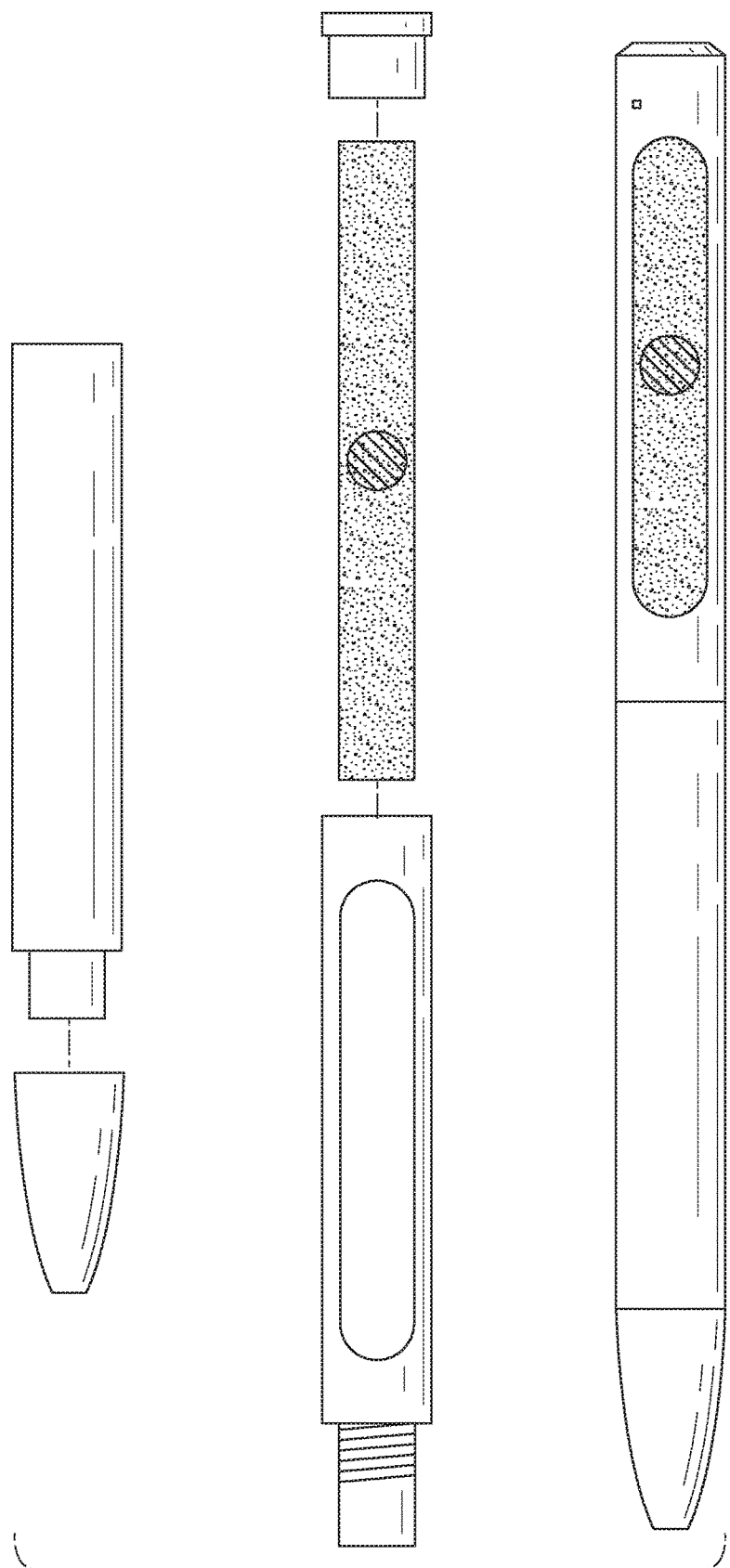
FIG. 6 is an expanded view of a fidget device, illustrating, in particular, a movable, manipulable object disposed within a sleeve of the writing instrument that a holder of the device can move back-and-forth and otherwise manipulate through movement within the sleeve, according to an embodiment of the invention.

Before describing the disclosed embodiments of this technology in detail, it is to be understood that the technology is not limited in its application to the details of the particular arrangement shown here since the technology described is capable of other embodiments. Also, the terminology used herein is for the purpose of description and not of limitation.

In various exemplary embodiments, the technology described herein provides a fidget device 10. The fidget device 10 is configured to direct a user to engage in a stress-release activity and direct nervous energy in a manner to not create distraction and noise. The technology provides a fidget device 10 having a movable, manipulable object 16 disposed within a sleeve 14 that a user can move back-and-forth and otherwise manipulate through movement within the sleeve 14.

Referring now to the Figures, a fidget device 10 is shown. The fidget device 10 has a sleeve 14 and a movable, manipulable object 16 disposed within the sleeve 14 that a holder of the fidget device 10 can move back-and-forth and otherwise manipulate through movement within the sleeve 14.

The fidget device 10 is configured to direct a user to engage in a stress-release activity and direct nervous energy in a manner to not create distraction and noise while used to aid attention, focus, calming, listening, and otherwise directing nervous energy.

In at least one embodiment, the fidget device is a writing instrument, such as a traditional pen, with a small movable object, such as a marble or ball bearing, disposed within that is used to roll in a back-and-forth motion with the fingers of the device holder to relieve stress and nervous energy.

In at least one embodiment, the fidget device 10—also provides that the movable object 16 is disposed within a woven mesh sleeve 14. A user or holder of the device can push the movable object, such as a marble, back and forth or squish the sleeve together to roll the object around with fingers, thereby to direct nervous energy in a less distracting way and in a more socially appropriate way.

In various alternative embodiments, the fidget device can be a pen, mechanical pencil, highlighter, marker, stylus, laser pointer, and so forth.

In at least one embodiment, the fidget device is non-retractable.

In at least one embodiment, the fidget device is retractable, wherein the ball goes through the ink cartridge depending on whether it is a short or long ink cartridge. The traditional pen can include the ink cylinder 24, a pen tip 22, a gripping cylinder 20, a ring 18, disposed between the upper and lower portions of the pen, a clip, and a cap 12.

In at least one embodiment, the fidget device 10 includes more than one movable object 16 disposed within, and they are all the same in size and shape.

In at least one embodiment, the fidget device 10 includes more than one movable object 16 disposed within, and they are all varied in size and shape.

In at least one embodiment, the fidget pen writing device is half twist.

In at least one embodiment, the fidget pen writing device is tip twist.

In at least one embodiment, the fidget device 10 is twisted at any location of the device.

In at least one embodiment, the fidget device 10 is integrally formed and all one piece with the exception of the movable object 16 disposed within.

In at least one embodiment, the fidget device 10 includes refillable ink.

In at least one embodiment, the fidget device 10 includes non-refillable ink.

In at least one embodiment, the fidget device 10 includes a cap 12.

In at least one embodiment, the fidget device 10 does not include a cap.

In at least one embodiment, the sleeve of the fidget device 10 is interchangeable.

In various embodiments, the sleeve 14 can twist, screw, or clip on.

In various embodiments, the sleeve 14 is flexible and can bend, roll, twist, or squish, or provide more than one of these functions.

In at least one embodiment, the sleeve 14 is mesh.

In at least one embodiment, the fidget device is foldable.

In at least one embodiment, the fidget device includes an outer sleeve with mesh, or the like, disposed within and within the mesh the movable object is disposed.

Although this technology has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the invention and are intended to be covered by the following claims.

What is claimed is:

1. A fidget writing device:
   a writing device;
   a mesh sleeve disposed within the writing device; and
   a movable, manipulable object disposed within the mesh sleeve that is movable back-and-forth and manipulable within the mesh sleeve.

2. The fidget writing device of claim 1, wherein the device is configured to direct a user to engage in a silent stress-release activity and direct nervous energy in a silent manner.

3. The fidget writing device of claim 1, wherein the fidget writing device comprises a writing instrument that is additionally configured as a fidget device and the sleeve and the movable, manipulable object are disposed within at least a portion of the writing instrument.

4. The fidget writing device of claim 1, wherein the movable, manipulable object comprises a marble.

5. The fidget writing device of claim 1, wherein the movable, manipulable object comprises a ball bearing.

6. The fidget writing device of claim 1, wherein the fidget device comprises one from the list of a pen, a pencil, a mechanical pencil, a highlighter, a marker, a stylus, and a laser pointer.

7. The fidget writing device of claim 1, wherein the fidget writing device is a pen and is non-retractable.

8. The fidget writing device of claim 1, wherein the fidget writing device comprises more than one movable object disposed within, and the movable objects are all the same in size and shape.

9. The fidget writing device of claim 1, wherein the fidget writing device comprises more than one movable object disposed within, and the movable objects are all varied in size and shape.

10. The fidget writing device of claim 1, wherein the fidget writing device is half twist.

11. The fidget writing device of claim 1, wherein the fidget writing device is tip twist.

12. The fidget writing device of claim 1, wherein the fidget writing device is twisted at any location of the device.

13. The fidget writing device of claim 1, wherein the fidget writing device is integrally formed and all one piece with the exception of the movable object disposed within.

14. The fidget writing device of claim 1, wherein the sleeve of the fidget device is interchangeable.

15. The fidget writing device of claim 1, wherein the sleeve is flexible and can bend, roll, twist, or squish.

16. The fidget writing device of claim 1, wherein the sleeve can twist, screw, and clip on.

17. The fidget writing device of claim 1, wherein the fidget writing device is foldable.

* * * * *